(12) United States Patent
Hegg

(10) Patent No.: US 7,744,643 B2
(45) Date of Patent: Jun. 29, 2010

(54) DISPLACEABLE STENT SIDE BRANCH STRUCTURE

(75) Inventor: Jens Hegg, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 98 days.

(21) Appl. No.: 11/417,466

(22) Filed: May 4, 2006

(65) Prior Publication Data

US 2007/0260303 A1 Nov. 8, 2007

(51) Int. Cl.
*A61F 2/06* (2006.01)
(52) U.S. Cl. .................................... 623/1.35
(58) Field of Classification Search ........ 623/1.15–1.17, 623/1.22, 1.35
See application file for complete search history.

(56) References Cited

U.S. PATENT DOCUMENTS

| | | | |
|---|---|---|---|
| 6,013,091 A | 1/2000 | Ley et al. ............... | 606/191 |
| 6,017,363 A | 1/2000 | Hojeibane ............... | 623/1 |
| 6,030,414 A | 2/2000 | Taheri ................... | 623/1 |
| 6,033,433 A | 3/2000 | Ehr et al. ............... | 623/1 |
| 6,048,361 A | 4/2000 | Von Oepen ............. | 623/1 |
| 6,056,775 A | 5/2000 | Borghi et al. ........... | 623/1.16 |
| 6,129,754 A | 10/2000 | Kanesaka et al. ....... | 623/1 |
| 6,210,429 B1 | 4/2001 | Vardi et al. ............. | 623/1.11 |
| 6,258,116 B1 | 7/2001 | Hojeibane ............... | 623/1.16 |
| 6,290,673 B1 | 9/2001 | Shanley ................. | 604/102.02 |
| 6,325,826 B1 | 12/2001 | Vardi et al. ............. | 623/1.35 |
| 6,334,870 B1 | 1/2002 | Ehr et al. ............... | 623/1.16 |
| 6,361,555 B1 | 3/2002 | Wilson ................... | 623/1.11 |
| 6,428,570 B1 * | 8/2002 | Globerman ............. | 623/1.15 |
| 6,436,134 B2 | 8/2002 | Richter et al. .......... | 673/1.15 |
| 6,579,309 B1 | 6/2003 | Loos et al. .............. | 623/1.16 |
| 6,582,394 B1 | 6/2003 | Reiss et al. ............. | 604/96.01 |
| 6,695,877 B2 | 2/2004 | Brucker et al. ......... | 623/1.16 |
| 6,706,062 B2 | 3/2004 | Vardi ..................... | 623/1.15 |
| 6,749,628 B1 | 6/2004 | Callol et al. ............ | 623/1.15 |

(Continued)

FOREIGN PATENT DOCUMENTS

WO 2004026180 4/2004

(Continued)

OTHER PUBLICATIONS

U.S. Appl. No. 11/300,210, filed Dec. 14, 2005, Eidenschink et al.

*Primary Examiner*—Suzette J Gherbi
(74) *Attorney, Agent, or Firm*—Vidas, Arrett & Steinkraus, P.A.

(57) ABSTRACT

In at least one embodiment, a stent comprises a side branch structure having an inner crown, an outer crown and a plurality of side branch connectors, each side branch connector connecting between the inner crown and the outer crown. Upon expansion of the side branch structure, the inner crown displaces outwardly in a stent radial direction. The entire inner crown moves out of the area defined by the generally cylindrical framework of the main stent body. Upon the outward displacement of the inner crown, the side branch connectors may reorient and also extend out of the area defined by the generally cylindrical framework of the main stent body. The inner crown may further comprise a plurality of outwardly deployable petals. Desirably, side branch expansion forces placed on the inner crown will first cause the inner crown to displace outwardly, then cause the petals to deploy outwardly.

17 Claims, 10 Drawing Sheets

U.S. PATENT DOCUMENTS

| | | | |
|---|---|---|---|
| 6,835,203 B1 | 12/2004 | Vardi et al. | 623/1.34 |
| 6,955,687 B2 | 10/2005 | Richter et al. | 623/1.35 |
| 7,341,598 B2 * | 3/2008 | Davidson et al. | 623/1.35 |
| 2001/0056297 A1 | 12/2001 | Hojeibane | 623/1.16 |
| 2002/0035392 A1 | 3/2002 | Wilson | 623/1.11 |
| 2002/0193873 A1 | 12/2002 | Brucker et al. | 623/1.35 |
| 2003/0195606 A1 * | 10/2003 | Davidson et al. | 623/1.11 |
| 2004/0138737 A1 | 7/2004 | Davidson et al. | 623/1.35 |
| 2004/0267352 A1 | 12/2004 | Davidson et al. | 623/1.15 |
| 2005/0010278 A1 | 1/2005 | Vardi et al. | 623/1.15 |
| 2005/0060027 A1 | 3/2005 | Khenansho et al. | 623/1.35 |
| 2005/0102023 A1 | 5/2005 | Yadin et al. | 623/1.15 |
| 2005/0119731 A1 | 6/2005 | Brucker et al. | 623/1.35 |
| 2005/0131526 A1 | 6/2005 | Wong | 623/1.15 |
| 2005/0154444 A1 | 7/2005 | Quadri | 623/1.13 |

FOREIGN PATENT DOCUMENTS

| | | |
|---|---|---|
| WO | 2005009295 | 2/2005 |

* cited by examiner

DISPLACEABLE STENT SIDE BRANCH STRUCTURE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs capable of supporting both a parent vessel and a branch vessel.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

U.S. Pat. No. 6,706,062 to Vardi et al. is incorporated herein by reference in its entirety. U.S. patent application Ser. No. 11/300,210 is incorporated herein by reference in its entirety. All other US patents, US applications and all other published documents mentioned anywhere in this application are also incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of struts arranged to form a substantially cylindrical expandable framework. The struts further define a plurality of cells and a side branch structure comprising an outer crown, an inner crown and a plurality of side branch connectors. The outer crown comprises a plurality of outer crown struts arranged to form a closed loop, the outer crown defining a side branch area. The inner crown comprises a plurality of inner crown struts arranged to form a closed loop, the inner crown defining an inner side branch cell having a shape different from the shape of any other cell. Each side branch connector has a first end connected to the inner crown and a second end connected to the outer crown. Upon expansion of said side branch structure, the entire inner crown displaces outwardly from said cylindrical expandable framework in a stent radial direction.

In at least one other embodiment, a stent comprises a plurality of struts arranged to form a substantially cylindrical expandable framework. The struts further define a plurality of cells and a side branch structure comprising an outer crown, an intermediate crown, an inner crown, a plurality of outer side branch connectors and a plurality of inner side branch connectors. The outer crown comprises a plurality of outer crown struts arranged to form a closed loop, the outer crown defining a side branch area. The intermediate crown comprises a plurality of intermediate crown struts arranged to form a closed loop, the intermediate crown oriented within the outer crown. Each outer side branch connector has a first end connected to the intermediate crown and a second end connected to the outer crown. The inner crown comprises a plurality of inner crown struts arranged to form a closed loop, the inner crown defining an inner side branch cell having a shape different from the shape of any other cell, the inner crown oriented within the intermediate crown. Each inner side branch connector has a first end connected to the inner crown and a second end connected to the intermediate crown. Upon a first expansion step of said side branch structure, the entire inner crown displaces outwardly from said cylindrical expandable framework in a stent radial direction. In some embodiments, the entire intermediate crown displaces outwardly from said cylindrical expandable framework in a stent radial direction upon said first expansion step. In some embodiments, the entire inner crown displaces outwardly from said intermediate crown in a stent radial direction during a second expansion step.

The stents may be placed with in a bodily vessel at a bifurcation and expanded to support the vessel(s). In some embodiments, the inner crown and side branch connectors, when expanded, extend into a bifurcation or branch vessel and provide scaffolding support to the branch vessel.

The invention further comprises methods of expanding the side branch structure of stents as described herein.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

Figure 1:
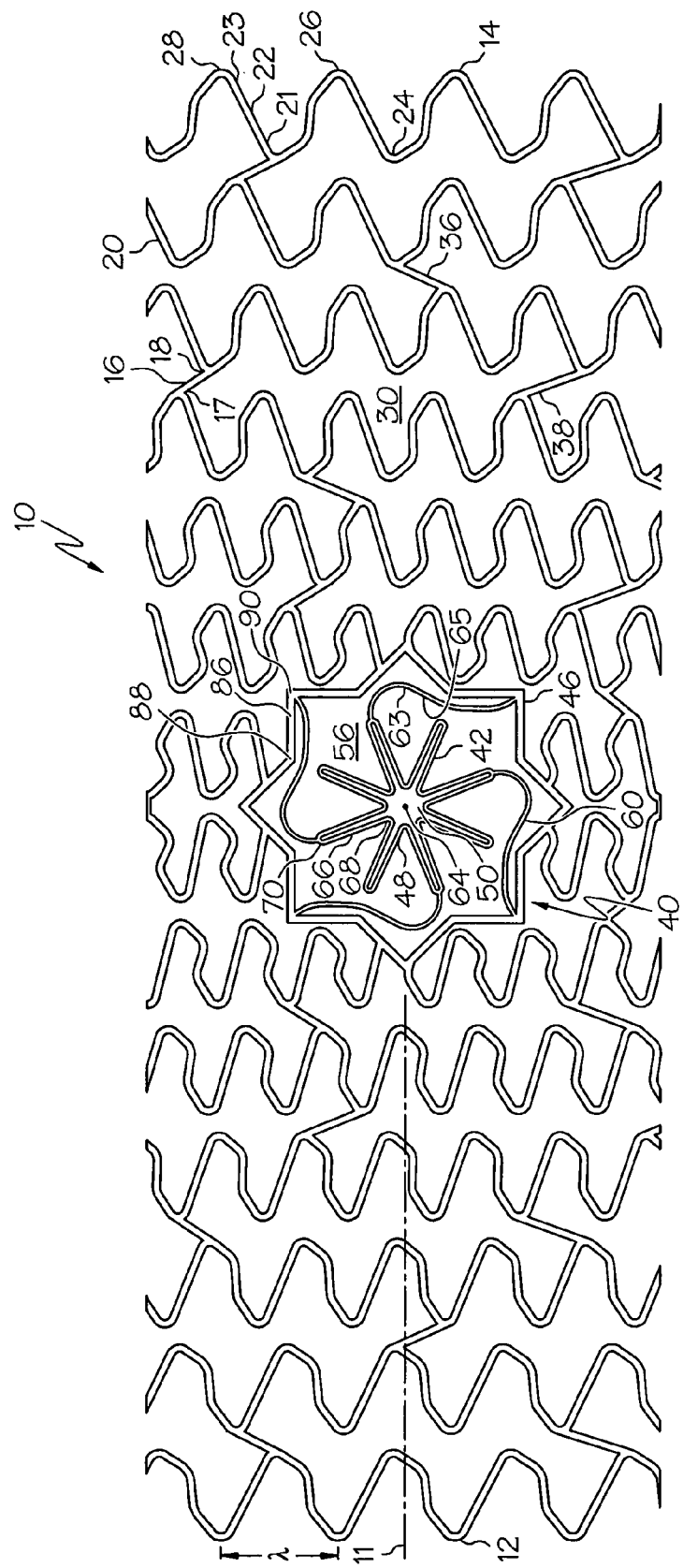
FIG. 1 shows an embodiment of a flat pattern for a stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

In some embodiments, a stent 10 comprises an outwardly expandable side branch structure that includes a crown structure having a plurality of outwardly deployable petals. The entire crown structure may displace radially outwardly from the main body portion of the stent 10, and the petals may then deploy outwardly.

Figure 2:
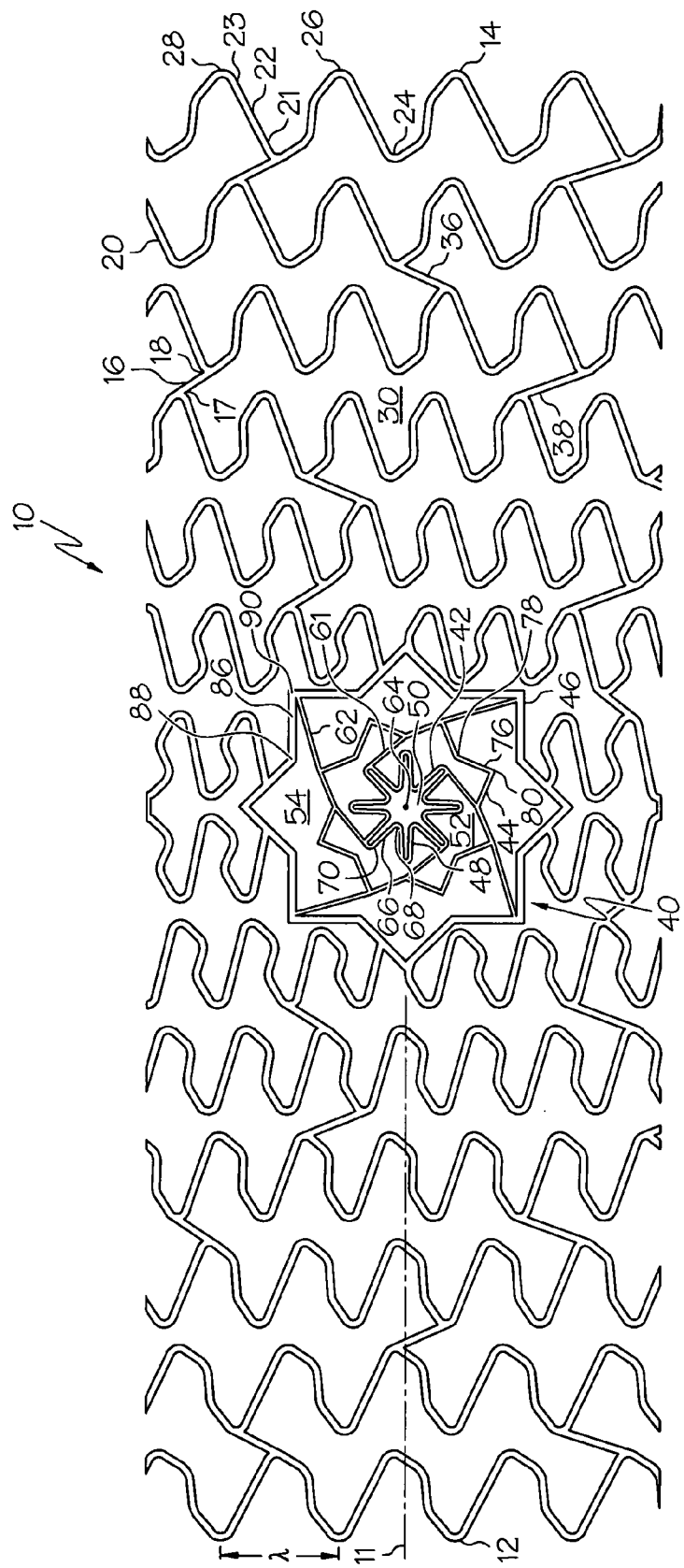
FIG. 2 shows another embodiment of a flat pattern for a stent.
Figure 3:
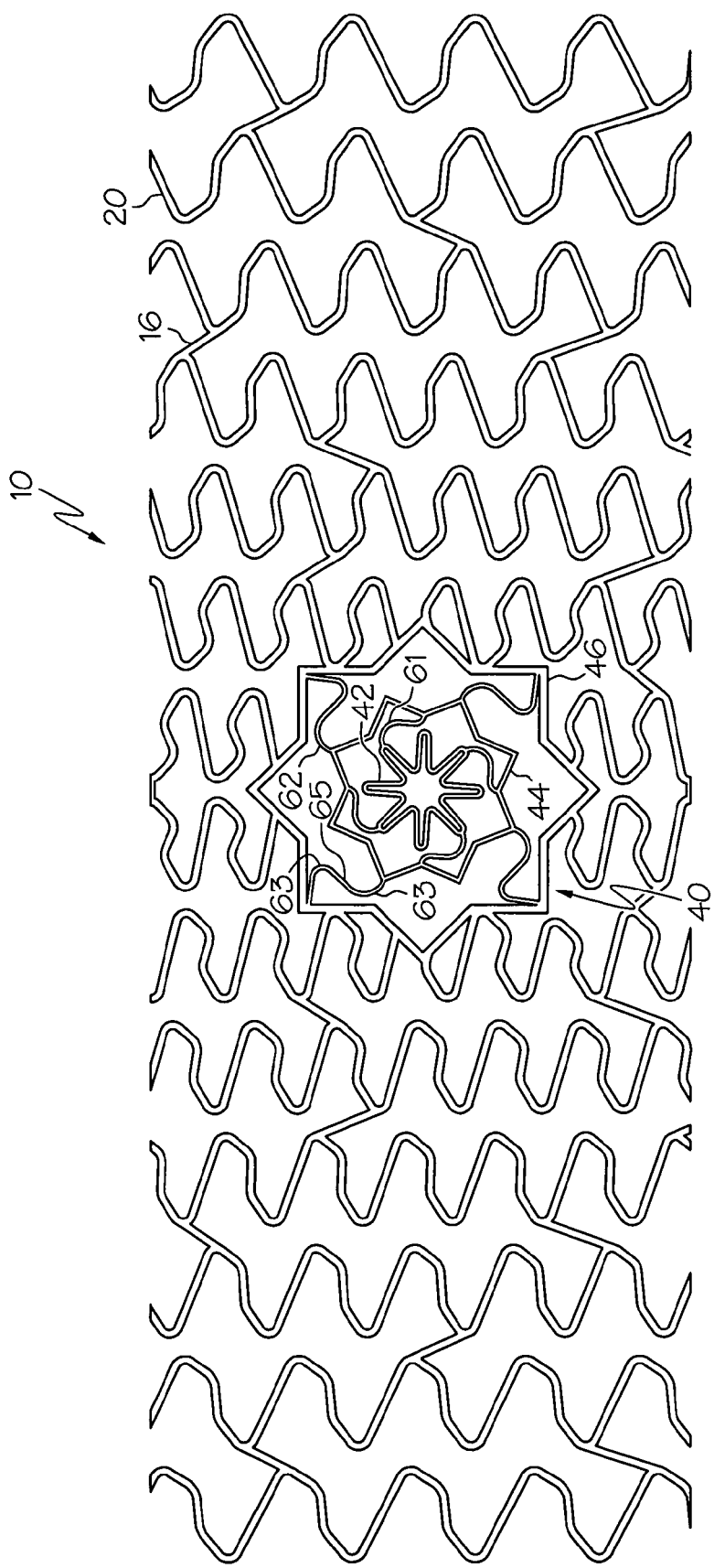
FIG. 3 shows another embodiment of a flat pattern for a stent.

Each of FIGS. 1-3 shows an embodiment of a flat pattern for a stent 10 having an outwardly expandable side branch structure 40. Each embodiment of a stent 10 comprises a plurality of strut members arranged to form a substantially cylindrical expandable framework. Each stent 10 embodiment has a proximal end 12, a distal end 14 and includes a plurality of serpentine bands 20. Each serpentine band 20 includes a plurality of struts 22, each strut 22 having a first end 21 and a second end 23. Circumferentially adjacent struts 22 within a serpentine band 20 are connected by turns 28. Turns 28 located on a proximal side of a serpentine band 20 comprise proximal peaks 24, and turns 28 located on a distal side of a serpentine band 20 comprise distal troughs or valleys 26.

Serpentine bands 20 which are adjacent to one another along the length of the stent 10 are connected by at least one connector strut 16. In some embodiments, a connector strut 16 may span between turns 28 of adjacent serpentine bands 20. For example, a first end 17 of a connector strut 16 may connect to a distal valley 26 of one serpentine band 20, and a second end 18 of the connector strut 16 may connect to a proximal peak 24 of an adjacent serpentine band 20.

Connector struts 16 may connect to any portion of a serpentine band 20, such as a turn 28, or in some embodiments, a strut 22. In some embodiments, a connector strut 16 may be linear or straight along its length. In some embodiments, a connector strut 16 may include curvature along its length, and may further include multiple portions of curvature, for example a convex portion and a concave portion that may be connected at an inflection point.

In some embodiments, a stent 10 may comprise a first type of connector strut 36 and a second type of connector strut 38. A first connector strut 36 may extend in a first direction. The first connector strut 36 may be oriented at a first angle to a stent lengthwise axis 11. A second connector strut 38 may extend in a second direction that is different than or non-parallel to the first direction. In some embodiments, the first angle and the second angle may have the same magnitude but different orientations.

A stent 10 may have any suitable number of serpentine bands 20. Each serpentine band 20 may have any suitable number of struts 22. In some embodiments, a serpentine band 20 may have a wavelength $\lambda$ or distance between repeating elements of the serpentine band 20. For example, a wavelength $\lambda$ may comprise a distance between adjacent proximal peaks 24 of a serpentine band 20, or a distance between adjacent distal valleys 26 of a serpentine band 20. In some embodiments, the wavelength $\lambda$ may change between adjacent serpentine bands 20. For example, the wavelength $\lambda$ of various serpentine bands 20 may be the shortest for serpentine bands 20 located near the center of the stent 10, and may increase as the stent 10 is traversed toward either end 12, 14. Adjacent serpentine bands 20 may further comprise different numbers of struts 22 and different numbers of turns 28.

In some embodiments, a serpentine band 20 extends about an entire circumference of the stent 10. For example, serpentine bands 20 that are offset from the side branch structure 40 may generally extend about an entire circumference of the stent 10. In some embodiments, a serpentine band 20 extends about a portion of a circumference of the stent 10. For example, serpentine bands 20 that connect to the side branch structure 40 may extend about a portion of a circumference of the stent 10.

A stent 10 may further comprise a plurality of cells 30. A cell 30 may comprise an opening in the stent 10 expandable framework between serpentine bands 20 and connector struts 16. In some embodiments, a cell 30 may be bounded by a serpentine band 20, a connector strut 16, another serpentine band 20 and another connector strut 16.

Referring to FIG. 1, a stent 10 may further comprise a side branch structure 40, which may define an inner crown 42, an outer crown 46 and a plurality of side branch connectors 60. The side branch structure 40 may be generally centered about a side branch center point 64. The inner crown 42 may define an inner side branch cell 50 which may be shaped differently than any other cell 30 of the stent 10. The inner side branch cell 50 may be generally centered upon the side branch center point 64.

The inner crown 42 may have any suitable shape and may form a closed loop that extends around the side branch center point 64. In some embodiments, the inner crown 42 may comprise a plurality of inner crown struts 66 connected between alternating inner crown inner turns 68 and inner crown outer turns 70. The inner crown inner turns 68 are located closer to the side branch center point 64 than the inner crown outer turns 70.

In some embodiments, each inner crown inner turn 68 may be aligned about a reference circle centered upon the side branch center point 64, and each inner crown outer turn 70 may be aligned upon another reference circle centered upon the side branch center point 64. Thus, each inner crown inner turn 68 may be located the same distance from the side branch center point 64 as all other inner crown inner turns 68, and each inner crown outer turn 70 may be located the same distance from the side branch center point 64 as all other inner crown outer turns 70.

In some embodiments, a peak of an inner crown inner turn 68 may point radially inwardly toward the side branch center point 64. A peak of an inner crown outer turn 70 may point radially outwardly away from the side branch center point 64.

Each inner crown strut 66 is connected at one end to an inner crown inner turn 68 and at another end to an inner crown outer turn 70. Each inner crown strut 66 may be straight along its length and may be oriented substantially parallel to a side branch radial direction.

The inner crown 42 defines a plurality of petals 48, each petal 48 comprising two inner crown struts 66 connected by an inner crown inner turn 68. Each petal 48 may unfold outwardly upon expansion of the side branch structure 40 and deployment of said petals 48 as described herein below and illustrated, for example, in FIGS. 5-6 and 9-10.

The outer crown 46 may have any suitable shape and may form a closed loop that extends around the inner crown 42. The outer crown 46 may be centered about the side branch center point 64.

In some embodiments, the outer crown 46 may comprise a plurality of outer crown struts 86 connected between alternating outer crown inner turns 88 and outer crown outer turns 90. Each outer crown strut 86 is connected at one end to an outer crown inner turn 88 and at another end to an outer crown outer turn 90. Each outer crown strut 86 may be straight along its length. Each outer crown strut 86 may have any suitable cross-sectional area, and in some embodiments, the cross-sectional area of an outer crown strut 86 may be equal to or greater than the cross-sectional area of an inner crown strut 66. In some embodiments, an outer crown 46 may have the same number of inner turns 88 and outer turns 90 as the inner crown 42.

The outer crown inner turns 88 are located closer to the side branch center point 64 than the outer crown outer turns 90. Each outer crown inner turn 88 may be aligned about a reference circle centered upon the side branch center point 64, and each outer crown outer turn 90 may be aligned upon another reference circle centered upon the side branch center point 64. Thus, each outer crown inner turn 88 may be located the same distance from the side branch center point 64 as all other outer crown inner turns 88, and each outer crown outer turn 90 may be located the same distance from the side branch center point 64 as all other outer crown outer turns 90. In some embodiments, a peak of an outer crown inner turn 88 may point radially inwardly toward the side branch center point 64. A peak of an outer crown outer turn 90 may point radially outwardly away from the side branch center point 64.

In some embodiments, inner crown turns 68, 70 may be aligned with outer crown turns 88, 90 in a side branch radial direction. For example, as shown in FIG. 1, inner crown outer turns 70 may be aligned with outer crown inner turns 88, and inner crown inner turns 68 may be aligned with outer crown outer turns 90 in a side branch radial direction. In other embodiments, inner crown outer turns 70 may be aligned with outer crown outer turns 90, and inner crown inner turns 68 may be aligned with outer crown inner turns 88 in a side branch radial direction. It should be noted that such alignment may change during side branch expansion, as the inner crown 42 may rotate with respect to the outer crown 46 during side branch expansion as described herein below.

In some embodiments, the length of inner crown struts 66 may be greater than the length of outer crown struts 86. In some embodiments, the length of a perimeter of the inner crown 42 may be equal to or greater than the length of a perimeter of the outer crown 46. Desirably, when comparing perimeter lengths, the inner crown 42 and the outer crown 46 are measured at corresponding and/or similar locations. For example, inner perimeter measurements or outer perimeter measurements may be taken for both the inner crown 42 and the outer crown 46.

The side branch structure 40 further comprises a plurality of side branch connectors 60. Each side branch connector 60 connects to the outer crown 46 at one end and to the inner crown 42 at the other end. A side branch connector 60 may have any suitable size, shape and cross-sectional area. In some embodiments, the cross-sectional area of a side branch connector 60 is less than the cross-sectional area of an inner crown strut 66.

In some embodiments, each side branch connector 60 may have a similar shape, and in some other embodiments, various side branch connectors 60 may have different shapes. A side branch connector 60 may have curvature along its length, and thus may include at least one peak 63. In some embodiments, a side branch connector 60 may include multiple peaks 63 along its length, which may have different orientations and may be located on opposite sides of an inflection point 65. In some embodiments, a side branch connector 60 may have at least a portion of its length, or all of its length, oriented in a side branch non-radial direction when the side branch structure 40 is unexpanded. The side branch connectors 60 may reorient upon expansion of the side branch structure 40.

Each side branch connector 60 may connect to any portion of the outer crown 46 and to any portion of the inner crown 42. In some embodiments, side branch connectors 60 connect to turns 68, 70, 88, 90 of the inner crown 42 and the outer crown 46. In some embodiments, a side branch connector 60 connects between an outer crown outer turn 90 and an inner crown outer turn 70. In some embodiments, each side branch connector 60 is oriented such that a first end and a second end of a given connector 60 are not aligned in a side branch radial direction.

The side branch structure 40 further defines a plurality of side branch cells 56. In some embodiments, a side branch cell 56 may be bounded by a portion of the inner crown 42, a side branch connector 60, a portion of the outer crown 46 and another side branch connector 60.

In some embodiments, each side branch cell 56 may have a similar shape. In some embodiments, the shape of one side branch cell 56 may comprise the shape of another side branch cell 56 rotated about the side branch center point 64, for example being rotated by 90°, 180° and/or 270°.

Expansion characteristics of the side branch structure 40 are discussed below with respect to FIGS. 4-6.

FIG. 2 shows another embodiment of a flat pattern for a stent 10 having a side branch structure 40. The side branch structure 40 may comprise an inner crown 42, an intermediate crown 44, a plurality of inner side branch connectors 61, an outer crown 46 and a plurality of outer side branch connectors 62. The side branch structure 40 may be generally centered about a side branch center point 64.

The inner crown 42 may be similar to the inner crown 42 as described with respect to FIG. 1, and thus may comprise inner crown struts 66, inner crown turns 68, 70 and petals 48.

The intermediate crown 44 may have any suitable shape and may form a closed loop that extends around the inner crown 42. The intermediate crown 44 may be centered about the side branch center point 64.

In some embodiments, the intermediate crown 44 may comprise a plurality of intermediate crown struts 76 connected between alternating intermediate crown inner turns 78 and intermediate crown outer turns 80. Each intermediate crown strut 76 is connected at one end to an intermediate crown inner turn 78 and at another end to an intermediate crown outer turn 80. Each intermediate crown strut 76 may be straight along its length. Each intermediate crown strut 76 may have any suitable cross-sectional area, and in some embodiments, the cross-sectional area of an intermediate crown strut 76 may be equal to or greater than the cross-sectional area of an inner crown strut 66. In some embodiments, an intermediate crown 44 may have the same number of inner turns 88 and outer turns 80 as the inner crown 42.

The intermediate crown inner turns 78 are located closer to the side branch center point 64 than the intermediate crown outer turns 80. Each intermediate crown inner turn 78 may be aligned about a reference circle centered upon the side branch center point 64, and each intermediate crown outer turn 80 may be aligned upon another reference circle centered upon the side branch center point 64. Thus, each intermediate crown inner turn 78 may be located the same distance from the side branch center point 64 as all other intermediate crown inner turn 78, and each intermediate crown outer turn 80 may be located the same distance from the side branch center point 64 as all other intermediate crown outer turns 80. In some embodiments, a peak of an intermediate crown inner turn 78 may point radially inwardly toward the side branch center point 64. A peak of an intermediate crown outer turn 80 may point radially outwardly away from the side branch center point 64.

In some embodiments, inner crown turns 68, 70 may be aligned with intermediate crown turns 78, 80 in a side branch radial direction. For example, as shown in FIG. 2, inner crown outer turns 70 may be aligned with intermediate crown inner turns 78, and inner crown inner turns 68 may be aligned with intermediate crown outer turns 80 in a side branch radial direction. In other embodiments, inner crown outer turns 70 may be aligned with intermediate crown outer turns 80, and inner crown inner turns 68 may be aligned with intermediate crown inner turns 78 in a side branch radial direction. It should be noted that such alignment may change during side branch expansion, as the inner crown 42 may rotate with respect to the intermediate crown 44 during side branch expansion as described herein below.

In some embodiments, the length of inner crown struts 66 may be greater than the length of intermediate crown struts 76. In some embodiments, the length of a perimeter of the inner crown 42 may be equal to or greater than the length of a perimeter of the intermediate crown 44. Desirably, when comparing perimeter lengths, the inner crown 42 and the intermediate crown 44 are measured at corresponding and/or similar locations. For example, inner perimeter measurements or outer perimeter measurements may be taken for both the inner crown 42 and the intermediate crown 44.

The outer crown 46 may have any suitable shape and may form a closed loop that extends around the intermediate crown 44. The outer crown 46 may be centered about the side branch center point 64. The outer crown 46 may be similar to the outer crown 46 as described with respect to FIG. 1, and thus may comprise outer crown struts 86, outer crown inner turns 88 and outer crown outer turns 90. In some embodiments, an outer crown 46 may have the same number of inner turns 88 and outer turns 90 as the intermediate crown 44.

In some embodiments, outer crown turns 88, 90 may be aligned with intermediate crown turns 78, 80 in a side branch radial direction. For example, as shown in FIG. 2, outer crown outer turns 90 may be aligned with intermediate crown inner turns 78, and outer crown inner turns 88 may be aligned with intermediate crown outer turns 80 in a side branch radial direction. In other embodiments, outer crown outer turns 90 may be aligned with intermediate crown outer turns 80, and outer crown inner turns 88 may be aligned with intermediate crown inner turns 78 in a side branch radial direction. It should be noted that such alignment may change during side branch expansion, as the intermediate crown 44 may rotate with respect to the outer crown 46 during side branch expansion as described herein below.

In some embodiments, the shape and orientation of the intermediate crown 44 may be chosen to maximize the size (i.e. distance across or diameter) of the intermediate crown 44 within the outer crown 46. In some embodiments, the shape and orientation of the intermediate crown 44 may further be chosen to allow a maximum amount of area within the intermediate crown 44, and thus may allow room to maximize the perimeter of the inner crown 42.

The side branch structure 40 comprises a plurality of inner side branch connectors 61. Each inner side branch connector 61 connects to the intermediate crown 44 at one end and to the inner crown 42 at the other end. An inner side branch connector 61 may have any suitable size, shape and cross-sectional area. In some embodiments, the cross-sectional area of an inner side branch connector 61 is less than the cross-sectional area of an inner crown strut 66. The cross-sectional area of an inner side branch connector 61 may also be less than the cross-sectional area of an intermediate crown strut 76.

In some embodiments, each inner side branch connector 61 may have a similar shape, and in some other embodiments, various inner side branch connectors 61 may have different shapes. As shown in FIG. 2, an inner side branch connector 61 may be straight along its length.

An inner side branch connector 61 may have at least a portion of its length, or all of its length, oriented in a side branch non-radial direction when the side branch structure 40 is unexpanded. The inner side branch connectors 61 may reorient upon expansion of the side branch structure 40.

Each inner side branch connector 61 may connect to any portion of the intermediate crown 44 and to any portion of the inner crown 42. In some embodiments, inner side branch connectors 61 connect to turns 68, 70, 78, 80 of the inner crown 42 and the intermediate crown 44. In some embodiments, an inner side branch connector 61 connects between an intermediate crown outer turn 80 and an inner crown outer turn 70. In some embodiments, an inner side branch connector 61 connects between an intermediate crown inner turn 78 and an inner crown outer turn 70.

The side branch structure 40 further defines a plurality of inner side branch cells 52. In some embodiments, an inner side branch cell 52 may be bounded by a portion of the inner crown 42, an inner side branch connector 61, a portion of the intermediate crown 44 and another inner side branch connector 61.

In some embodiments, each inner side branch cell 52 may have a similar shape. In some embodiments, the shape of one inner side branch cell 52 may comprise the shape of another inner side branch cell 52 rotated about the side branch center point 64, for example being rotated by 90°, 180° and/or 270°.

The side branch structure 40 comprises a plurality of outer side branch connectors 62. Each outer side branch connector 62 connects to the intermediate crown 44 at one end and to the outer crown 46 at the other end. An outer side branch connector 62 may have any suitable size, shape and cross-sectional area. In some embodiments, the cross-sectional area of an outer side branch connector 62 is less than the cross-sectional area of an intermediate crown strut 76.

In some embodiments, each outer side branch connector 62 may have a similar shape, and in some other embodiments, various outer side branch connectors 62 may have different shapes. As shown in FIG. 2, an outer side branch connector 62 may be straight along its length.

An outer side branch connector 62 may have at least a portion of its length, or all of its length, oriented in a side branch non-radial direction when the side branch structure 40 is unexpanded. The outer side branch connectors 62 may reorient upon expansion of the side branch structure 40.

Each outer side branch connector 62 may connect to any portion of the intermediate crown 44 and to any portion of the outer crown 46. In some embodiments, outer side branch connectors 62 connect to turns 78, 80, 88, 90 of the intermediate crown 44 and the outer crown 45. In some embodiments, an outer side branch connector 62 connects between an intermediate crown outer turn 80 and an outer crown outer turn 90.

In some embodiments, inner side branch connectors 61 and outer side branch connectors 62 may connect to intermediate crown outer turns 80. In some embodiments, an inner side branch connector 61 and an outer side branch connector 62 may connect to a common intermediate crown outer turn 80.

The side branch structure 40 further defines a plurality of outer side branch cells 54. In some embodiments, an outer side branch cell 54 may be bounded by a portion of the intermediate crown 44, an outer side branch connector 62, a portion of the outer crown 46 and another outer side branch connector 62.

In some embodiments, each outer side branch cell 54 may have a similar shape. In some embodiments, the shape of one outer side branch cell 54 may comprise the shape of another outer side branch cell 54 rotated about the side branch center point 64, for example being rotated by 90°, 180° and/or 270°.

FIG. 3 shows another embodiment of a flat pattern for a stent 10. The serpentine bands 20, connector struts 16, inner crown 42, intermediate crown 44 and outer crown 46 may be similar to the structure illustrated and described with respect to FIG. 2.

In some embodiments, the inner side branch connectors 61 and/or the outer side branch connectors 62 may include curvature and thus may include at least one peak 63. In some embodiments, a side branch connector 61, 62 may include multiple peaks 63 along its length, which may have different orientations and may be located on opposite sides of an inflection point 65.

Including curvature in the side branch connectors may allow for longer side branch connectors, and may allow for a longer side branch connector to be oriented within the area available between the various crowns 42, 44, 46.

Figure 4:
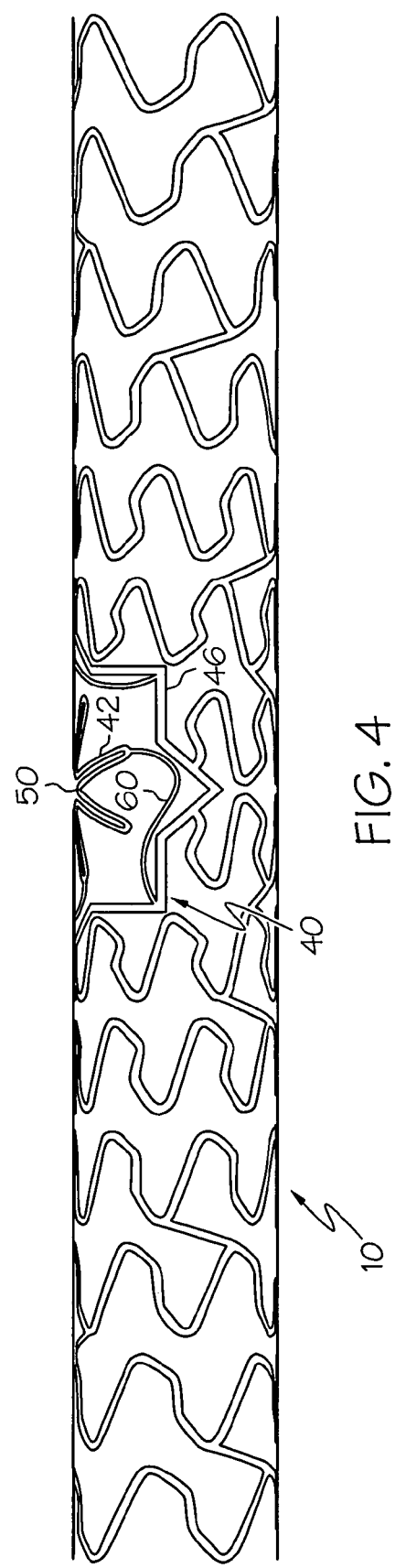
FIG. 4 shows a stent according to the embodiment of FIG. 1 with the side branch structure unexpanded.
Figure 5:
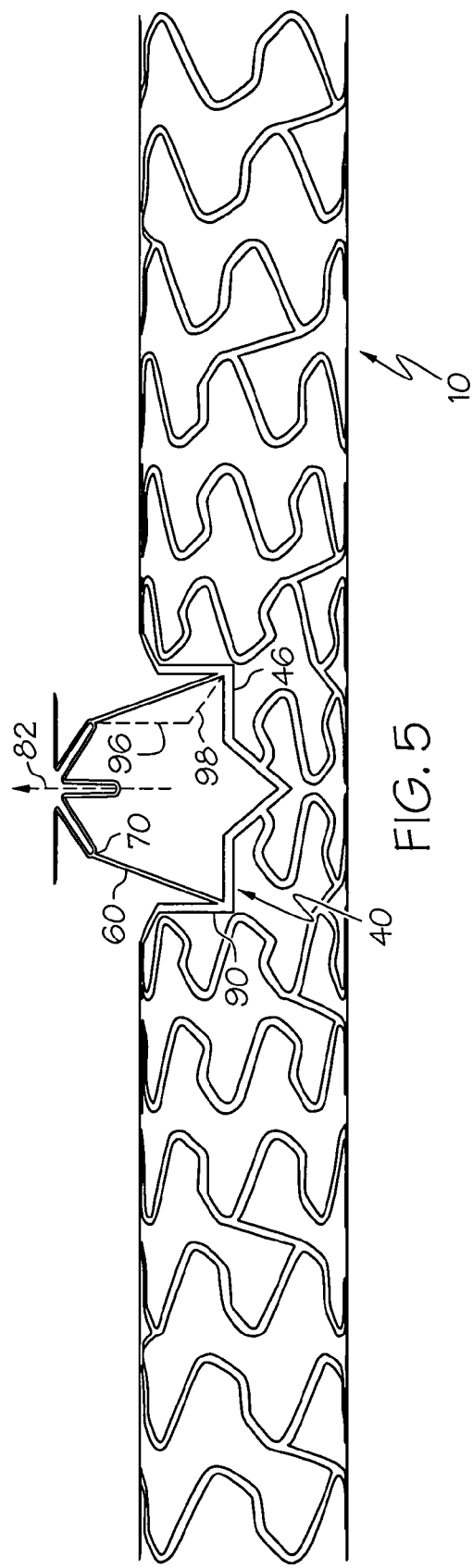
FIG. 5 shows the stent of FIG. 4 with the side branch structure in an expanded state.
Figure 6:
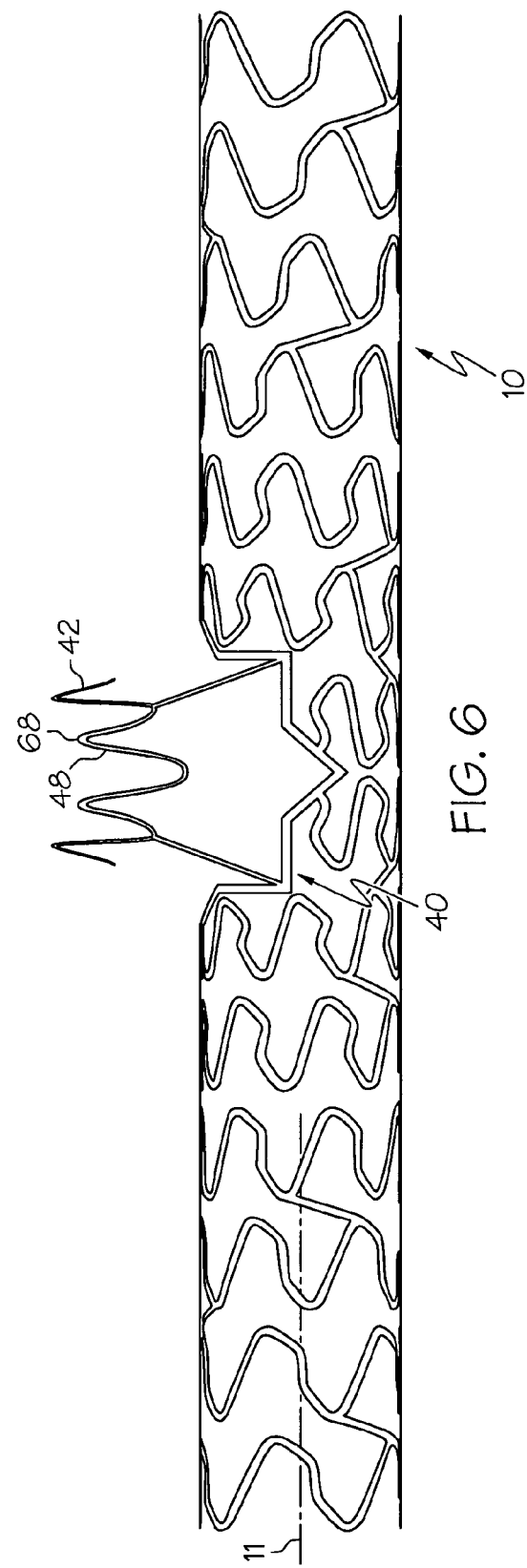
FIG. 6 shows the stent of FIG. 4 with the side branch structure expanded and the side branch petals outwardly deployed.

Referring to FIGS. 4-6, the stent 10 of FIG. 1 is shown at various stages of side branch expansion.

FIG. 4 shows the side branch structure 40 in a first or unexpanded state, wherein all of the side branch structure 40 is oriented within the area of the cylindrical plane defined by the substantially cylindrical framework of the stent 10. The area of the inner side branch cell 50 defined within the inner crown 42 overlaps the area defined within the outer crown 46. At least a substantial portion of the length of the side branch connectors 60 may be oriented in a side branch non-radial direction.

FIG. 5 shows the side branch structure 40 in a second or expanded state. The side branch structure 40 may be expanded, for example, by a catheter balloon or any other suitable side branch expansion device. In some embodiments, an expansion device may comprise a catheter balloon having an auxiliary inflatable portion, for example as disclosed in US Published Patent Application No. 2005/0060027 to Khenansho et al., the entire disclosure of which is hereby incorporated herein by reference in its entirety. The expansion device may place forces that are directed in a stent radial outward direction upon any portion of the side branch structure 40, and desirably upon the inner crown 42, and more desirably upon the inner crown struts 66 and inner crown inner turns 68.

During side branch expansion, the inner crown 42 displaces outwardly in a stent radial direction 82 and moves out of the area of the cylindrical plane defined by the substantially cylindrical framework of the stent 10. The stent radial direction 82 being referred to may pass through the side branch center point 64 (see FIG. 1). After the outward displacement, the area defined within the inner crown 42 does not overlap the area defined within the outer crown 46.

The inner crown 42 may further rotate with respect to the outer crown 46 and with respect to the rest of the stent 10 during side branch expansion. In some embodiments, an inner crown outer turn 70 that was not aligned with an outer crown outer turn 90 in a side branch radial direction prior to side branch expansion may become aligned with an outer crown outer turn 90 in a side branch radial direction as the inner crown 42 rotates.

The side branch connectors 60 reorient during side branch expansion and allow the inner crown 42 to displace outwardly. After side branch expansion, the side branch connectors 60 may extend out of the area of the cylindrical plane defined by the substantially cylindrical framework of the stent 10. The side branch connectors 60 may further be oriented, or may have a length component oriented, in a side branch radial direction. When three dimensions are taken into consideration, a line having a length component in the plane of the side branch structure oriented in a side branch radial direction may be described as being oriented in a side branch radial direction. Due to the three-dimensional nature of the stent 10, after side branch expansion a side branch connector 60 may have a first length component 96 that is oriented in a stent radial direction and a second length component 98 that is oriented in a side branch radial direction. In embodiments where the side branch connectors 60 include curvature, they may straighten upon side branch expansion.

FIG. 6 shows the side branch structure 40 in a third or deployed state, wherein each petal 48 defined by the inner crown 42 has unfolded outwardly. When the inner crown 42 has displaced outwardly in a stent radial direction the maximum amount allowed by the side branch connectors 60, continued outward force applied by the expansion device desirably causes the petals 48 to unfold. Each inner crown inner turn 68 may displace outward in both stent radial and side branch radial directions upon petal 48 deployment.

As shown in FIGS. 5 and 6, the outer crown 46 remains within the area of the cylindrical plane defined by the substantially cylindrical framework of the stent 10 throughout side branch expansion and petal 48 deployment.

In some embodiments, a side branch expansion device that applies outward forces to the inner crown 42 does not distinguish between the stages of expansion illustrated in FIGS. 4-6. Therefore, it is likely that similar forces applied by a similar portion of an expansion device will work to both displace the inner crown 42 outwardly and to unfold the petals 48.

The inner crown 42 and the side branch connectors 60 are desirably designed such that side branch expansion forces applied to the inner crown 42 will first work to displace the inner crown 42 outwardly. After the side branch connectors 60 have reoriented and the inner crown 42 is located at an outward displacement limit, the expansion forces then cause the petals 48 to unfold. Thus, the force required to unfold the petals 48 is desirably greater than the force required to displace the inner crown 42 and reorient the side branch connectors 60. The various members of the side branch structure 40 may be sized and shaped to create the strength gradient necessary for such side branch expansion/deployment, for example using finite element analysis.

Stents 10 as described herein may be used to support vessel walls. The main cylindrical framework may be used to support a main branch vessel wall. The expanded and deployed side branch structure may be used to support a branch vessel. In some embodiments, side branch connectors 60 may provide scaffolding support to portions of a branch vessel or area of bifurcation, such as the carina or contralateral ostial wall. The inner crown 42 and more specifically the outwardly deployed petals 48 may further provide scaffolding support for a branch vessel.

FIG. 6 shows a slight taper in the deployed side branch structure 40. The amount of taper may be adjusted in various embodiments to provide appropriate support for a side branch vessel. In various embodiments, the side branch structure 40 may be designed with a high amount of taper (i.e. the deployed diameter of the inner crown 42 is substantially smaller than that of the outer crown 46), no taper (i.e. the deployed diameter of the inner crown 42 is substantially equal to that of the outer crown 46), or even an outward taper (i.e. the deployed diameter of the inner crown 42 is larger than that of the outer crown 46). In some embodiments, the deployed inner crown 42 may further be stretched by an appropriate deployment device to increase its deployed diameter.

FIG. 6 further shows the expanded side branch structure 40 extending from the main cylindrical framework in a direction that is generally orthogonal to the central longitudinal axis 11 of the stent 10. In some embodiments, the expanded side branch structure may extend at a different angle to the stent 10 longitudinal axis in order to match the orientation of a branch vessel. In some embodiments, the collective general direction of extension of the side branch structure 40 may be adjusted by varying the length of individual side branch connectors 60. For example, if the side branch connectors 60 that connect to a proximal side of the outer crown 46 are longer than the side branch connectors 60 that connect to a distal side of the outer crown 46, the expanded side branch structure 40 may be angled in the distal direction.

Referring to FIGS. 7-10, the stent 10 of FIG. 3 is shown at various stages of side branch expansion.

Figure 7:
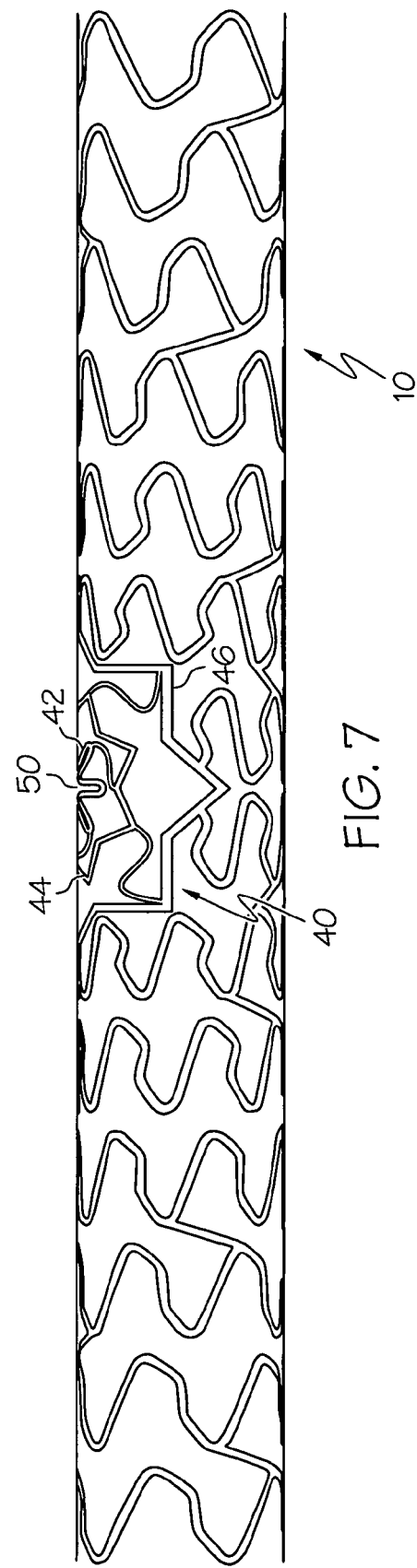
FIG. 7 shows a stent according to the embodiment of FIG. 3 with the side branch structure unexpanded.

FIG. 7 shows the side branch structure 40 in a first or unexpanded state, wherein all of the side branch structure 40 is oriented within the area of the cylindrical plane defined by the substantially cylindrical framework of the stent 10. The area of the inner side branch cell 50 defined within the inner crown 42 overlaps the area defined within the intermediate crown 44. The area defined within the intermediate crown 44 overlaps the area defined within the outer crown 46. At least a substantial portion of the length of the inner side branch connectors 61 and the outer side branch connectors 62 may be oriented in a side branch non-radial direction.

Figure 8:
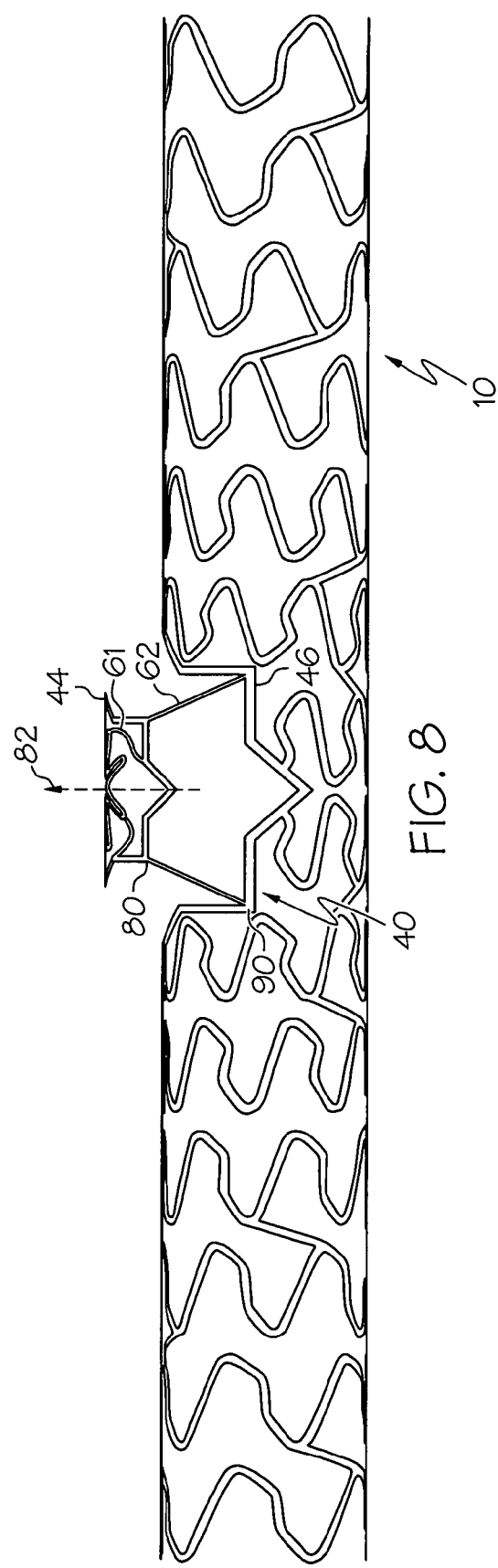
FIG. 8 shows the stent of FIG. 7 with the side branch structure partially expanded.

FIG. 8 shows the side branch structure 40 in a second or intermediate state following a first expansion step. An expansion device may place forces that are directed in a stent radial outward direction 82 upon any portion of the side branch structure 40, desirably upon the intermediate crown 44 and the inner crown 42, and more desirably upon the inner crown struts 66 and inner crown inner turns 68. The stent radial direction 82 being referred to may pass through the side branch center point 64 (see FIG. 3).

During side branch expansion, the intermediate crown 44, inner crown connectors 61 and the inner crown 42 displace outwardly in a stent radial direction, and move out of the area of the cylindrical plane defined by the substantially cylindrical framework of the stent 10. After the outward displacement, the area defined within the intermediate crown 44 and the area defined within the inner crown 42 do not overlap the area defined within the outer crown 46. The intermediate crown 44, inner crown connectors 61 and the inner crown 42 may further rotate with respect to the outer crown 46 and with respect to the rest of the stent 10 during side branch expansion. In some embodiments, an intermediate crown outer turn 80 that was not aligned with an outer crown outer turn 90 in a side branch radial direction prior to side branch expansion may become aligned with an outer crown outer turn 90 in a side branch radial direction as the intermediate crown 44 rotates.

The outer side branch connectors 62 reorient during side branch expansion and allow the intermediate crown 44 to displace outwardly. After the displacement, the outer side branch connectors 62 may extend out of the area of the cylindrical plane defined by the substantially cylindrical framework of the stent 10. The outer side branch connectors 62 may further have a length component oriented in a side branch radial direction and another length component oriented in a stent radial direction.

In embodiments where the outer side branch connectors 62 include curvature, they may straighten upon intermediate crown 44 outward displacement.

Figure 9:
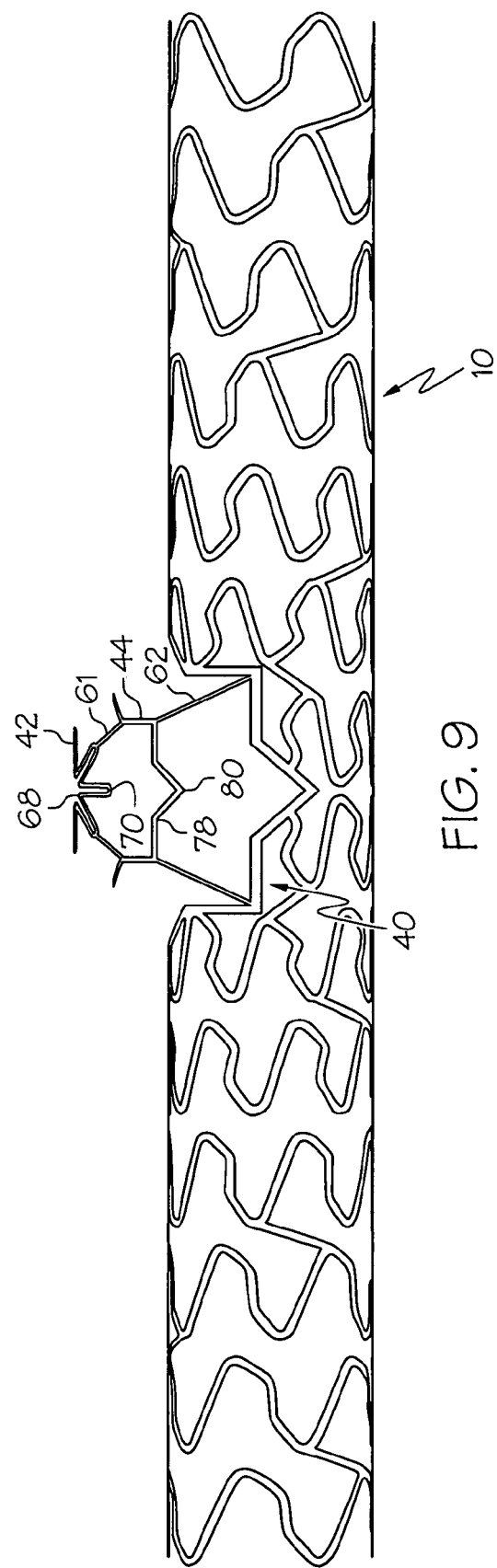
FIG. 9 shows the stent of FIG. 7 with the side branch structure in an expanded state.

FIG. 9 shows the side branch structure 40 in a third or expanded state following a second expansion step. The inner crown 42 is displaced outwardly in a stent radial direction and has moved out of the area defined within the intermediate crown 44.

The inner side branch connectors 61 have reoriented and now extend out of the area defined within the intermediate crown 44. The inner side branch connectors 61 may further have a length component oriented in a side branch radial direction and another length component oriented in a stent radial direction. In embodiments where the inner side branch connectors 61 include curvature, they may straighten as the inner crown 42 is displaced away from the intermediate crown 44.

The inner crown 42 may further rotate with respect to the intermediate crown 44 and with respect to the rest of the stent 10, and thus alignment between the inner crown turns 68, 70 and the intermediate crown turns 78, 80 may change during displacement of the inner crown 42. The inner crown 42 may further be arranged to rotate with respect to the intermediate crown 44 in the same direction that the intermediate crown 44 rotates with respect to the outer crown 46, or in a different direction. Having opposite rotational orientations may be desirable, for example in order to minimize cumulative rotational stresses experienced by an expansion device. The direction of rotation of either crown 42, 44 may be selected by varying the orientation and connection locations of the side branch connectors 61, 62.

In some embodiments, the structural changes described with respect to the above first and second expansion steps may occur in a different order. For example, in some embodiments, the inner crown 42 may first displace outward in a stent radial direction while the intermediate crown 44 remains within the area defined within the outer crown 46, and then the intermediate crown 44 may displace outwardly while the inner crown 42 continues to displace outwardly. In some embodiments, the intermediate crown 44 may displace outwardly from the outer crown 46 and the inner crown 42 may displace outwardly from the intermediate crown 44 simultaneously.

Figure 10:
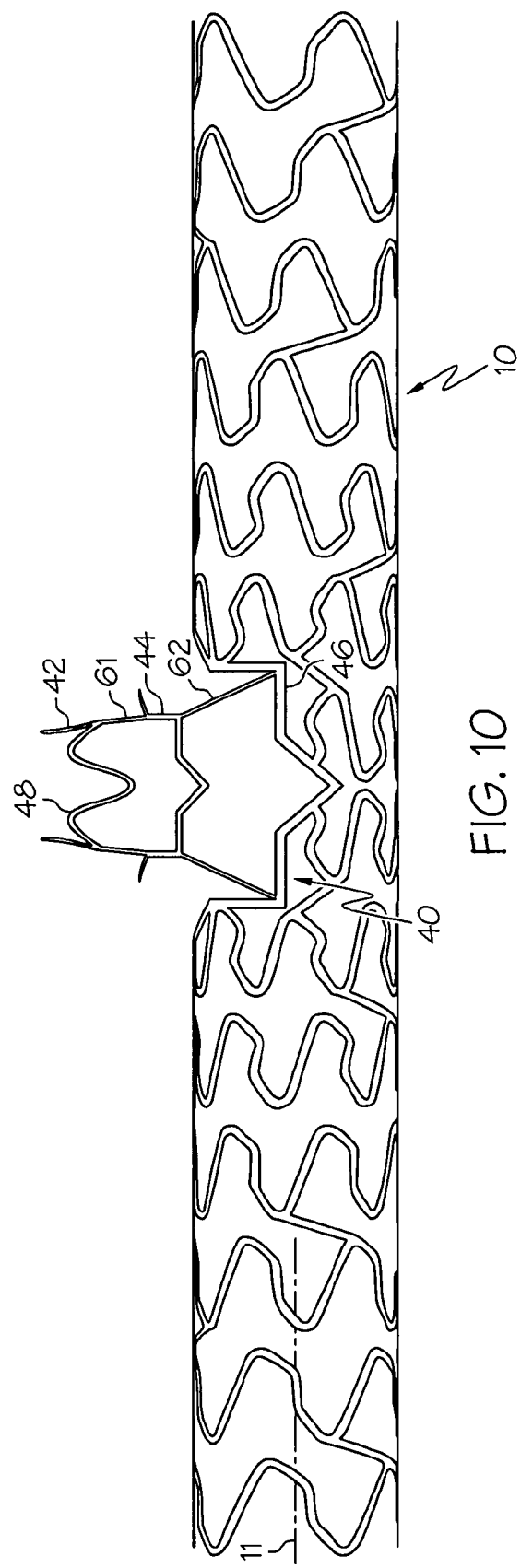
FIG. 10 shows the stent of FIG. 7 with the side branch structure expanded and the side branch petals outwardly deployed.

FIG. 10 shows the side branch structure 40 in a fourth or deployed state, wherein each petal 48 defined by the inner crown 42 has unfolded outwardly. When the inner crown 42 has displaced outwardly in a stent radial direction the maximum amount allowed by the inner side branch connectors 61 and the outer side branch connectors 62, continued outward force applied by the expansion device desirably causes the petals 48 to unfold. Each inner crown inner turn 68 may displace outward in both stent radial and side branch radial directions upon petal 48 deployment.

As shown in FIGS. 8-10, the outer crown 46 remains within the area of the cylindrical plane defined by the substantially cylindrical framework of the stent 10 throughout side branch expansion and petal 48 deployment.

The various inner crown 42, the inner side branch connectors 61 and the outer side branch connectors 62 are desirably designed such that side branch expansion forces applied to the inner crown 42 will first work to displace the inner crown 42 outwardly. After the side branch connectors 61, 62 have reoriented and the inner crown 42 is located at an outward displacement limit, the expansion forces then cause the petals 48 to unfold. Thus, the force required to unfold the petals 48 is desirably greater than the force required to displace the inner crown 42 and reorient the side branch connectors 61, 62. The various members of the side branch structure 40 may be sized to create the strength gradient necessary for proper side branch expansion/deployment, for example using finite element analysis. The strength of the inner side branch connectors 61 and the outer side branch connectors 62 may further be adjusted with respect to one another to influence the timing of displacement of the intermediate crown 44 with respect to the outer crown 46 and displacement of the inner crown 42 with respect to the intermediate crown 44.

Stents 10 as described herein may be used to support vessel walls. The main cylindrical framework may be used to support a main branch vessel wall. The expanded and deployed side branch structure may be used to support a branch vessel. In some embodiments, outer side branch connectors 62 may provide scaffolding support to portions of a branch vessel or area of bifurcation, such as the carina or contralateral ostial wall. The intermediate crown 44, the inner side branch connectors 61, the inner crown 42 and more specifically the outwardly deployed petals 48 may further provide scaffolding support for a branch vessel.

FIG. 10 shows a slight taper in the deployed side branch structure 40. The amount of taper may be adjusted in various embodiments to provide appropriate support for a side branch vessel. In various embodiments, the side branch structure 40 may be designed with a high amount of taper, no taper or even a reverse taper. The amount of taper may be adjusted by adjusting the size (i.e. diameter) of the outer crown 46, the intermediate crown 44 and the inner crown 42 with respect to one another. In some embodiments, the deployed inner crown 42 may further be stretched by an appropriate deployment device to increase its deployed diameter.

FIG. 10 further shows the expanded side branch structure 40 extending from the main cylindrical framework in a direction that is generally orthogonal to the central longitudinal axis 11 of the stent 10. In some embodiments, the expanded side branch structure 40 may extend at a different angle to the stent 10 longitudinal axis in order to match the orientation of a side branch vessel. In some embodiments, the collective general direction of extension of the side branch structure 40 may be adjusted by varying the length of individual inner side branch connectors 61 and outer side branch connectors 62. For example, if the outer side branch connectors 62 that connect to a proximal side of the outer crown 46 are longer than the inner side branch connectors 62 that connect to a distal side of the outer crown 46, the expanded side branch structure 40 may be angled in the distal direction. The inner side branch connectors 61 and the outer side branch connectors 62 may further be adjusted independently from one another. For example, using outer side branch connectors 62 of the same length and inner side branch connectors 61 of different lengths may provide the expanded side branch structure 40 with a curve.

In some embodiments, the side branch connectors 61, 62 may all connect between outer turns 70, 80, 90 of the various crown structures 42, 44, 46 in order to maximize the expanded diameter of the side branch structure 40.

The invention is further directed to methods of making stents 10 as described herein. The invention is further directed to methods of delivering and expanding/deploying stents 10 as described herein.

A stent 10 may be delivered to a deployment location, for example using a delivery catheter. In some embodiments, the stent 10 may be delivered to a vessel bifurcation and oriented such that the side branch structure 40 will extend into a branch vessel during side branch expansion. The substantially cylindrical framework of the stent 10 may be expanded in diameter, for example by inflating a catheter balloon. The side branch structure 40 may further be expanded and deployed as described herein using any suitable method, such as an auxiliary inflatable side branch portion of a balloon catheter.

In some embodiments, a stent 10 may be self-expanding, for example being made from a shape memory material. A self-expanding stent 10 may normally assume an expanded configuration wherein the side branch structure is expanded and deployed. A self-expanding stent 10 may be delivered to a deployment location in an unexpanded configuration, for example being constrained by a sheath. Upon removal of the constrainment device, the stent 10 may assume its expanded configuration.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The invention further comprises various embodiments of stents 10 as described in the following numbered paragraphs:

1. A stent comprising:
    a plurality of struts arranged to form a substantially cylindrical expandable framework, the struts defining a plurality of cells; and
    a side branch structure comprising:
        an outer crown comprising a plurality of outer crown struts arranged to form a closed loop, the outer crown defining a side branch area;
        an intermediate crown comprising a plurality of intermediate crown struts arranged to form a closed loop, the intermediate crown oriented within the outer crown;
        a plurality of outer side branch connectors, each outer side branch connector having a first end connected to the intermediate crown and a second end connected to the outer crown;
        an inner crown comprising a plurality of inner crown struts arranged to form a closed loop, the inner crown defining an inner side branch cell having a shape different from the shape of any other cell, the inner crown oriented within the intermediate crown; and
        a plurality of inner side branch connectors, each inner side branch connector having a first end connected to the inner crown and a second end connected to the intermediate crown;
    wherein upon a first expansion step of said side branch structure, the entire inner crown displaces outwardly from said cylindrical expandable framework in a stent radial direction.
2. The stent of paragraph 1, wherein the entire intermediate crown displaces outwardly from said cylindrical expandable framework in a stent radial direction upon said first expansion step.
3. The stent of paragraph 2, wherein upon a second expansion step, the entire inner crown displaces outwardly from said intermediate crown in a stent radial direction.
4. The stent of paragraph 3, wherein a first inner side branch connector is oriented in a side branch non-radial direction when said side branch structure is unexpanded.
5. The stent of paragraph 4, wherein said first inner side branch connector includes curvature along its length.
6. The stent of paragraph 4, wherein said first inner side branch connector reorients in a side branch radial direction upon said second expansion step of said side branch structure.
7. The stent of paragraph 3, wherein the inner crown further comprises a plurality of petals, each petal rotating to unfold outwardly in a stent radial direction upon petal deployment.
8. The stent of paragraph 7, wherein each petal unfolds outwardly in a side branch radial direction upon petal deployment.
9. The stent of paragraph 7, wherein a force applied to the stent by a catheter balloon required to displace the intermediate crown outwardly during the first expansion step is less than the force required to displace the inner crown outwardly with respect to the intermediate crown during the second expansion step.
10. The stent of paragraph 9, wherein the force required to displace the inner crown outwardly with respect to the intermediate crown during the second expansion step is less than the force required to unfold the petals outwardly during petal deployment.
11. The stent of paragraph 3, wherein the inner crown rotates with respect to the outer crown during said first expansion step.
12. The stent of paragraph 2, wherein the intermediate crown rotates with respect to the outer crown during said first expansion step.
13. The stent of paragraph 12, wherein the inner crown rotates with the intermediate crown during said first expansion step.
14. The stent of paragraph 3, wherein the inner crown rotates with respect to the intermediate crown during said second expansion step.
15. The stent of paragraph 1, wherein the inner crown rotates with respect to the outer crown during said first expansion step
16. The stent of paragraph 1, the side branch structure in an unexpanded state defining a plurality of outer side branch cells, each outer side branch cell being partially bounded by at least one outer crown strut, at least one intermediate crown strut, a first outer side branch connector and a second outer side branch connector.
17. The stent of paragraph 16, wherein the shape of an outer side branch cell comprises the shape of another outer side branch cell rotated about a side branch center point.
18. The stent of paragraph 16, the side branch structure further defining a plurality of intermediate side branch cells, each intermediate side branch cell being partially bounded by at least one intermediate crown strut, at least one inner crown strut, a first inner side branch connector and a second inner side branch connector.
19. The stent of paragraph 18, wherein the shape of an intermediate side branch cell comprises the shape of another intermediate side branch cell rotated about the side branch center point.
20. The stent of paragraph 1, wherein a perimeter of the inner crown is equal to or greater than a perimeter of the intermediate crown.
21. The stent of paragraph 1, wherein a perimeter of the inner crown is equal to or greater than a perimeter of the outer crown.
22. The stent of paragraph 1, wherein the outer crown remains in said cylindrical expandable framework after said first expansion step.
23. The stent of paragraph 3, wherein the outer crown remains in said cylindrical expandable framework after said second expansion step.
24. The stent of paragraph 1, wherein a first outer side branch connector is oriented in a side branch non-radial direction when said side branch structure is unexpanded.

25. The stent of paragraph 24, wherein said first outer side branch connector includes curvature along its length.
26. The stent of paragraph 24, wherein said first outer side branch connector reorients in a side branch radial direction upon said first expansion step.
27. The stent of paragraph 1, wherein a cross-sectional area of an inner crown strut is greater than a cross-sectional area of an inner side branch connector.
28. The stent of paragraph 1, wherein a cross-sectional area of an inner side branch connector is greater than a cross-sectional area of an outer side branch connector.
29. The stent of paragraph 1, the inner crown further comprising a plurality of inner crown inner turns and a plurality of inner crown outer turns, each inner crown strut connected at one end to an inner crown inner turn and at another end to an inner crown outer turn, the inner turns located closer to a side branch center point than the outer turns.
30. The stent of paragraph 29, wherein each inner crown outer turn is located an equal distance from the side branch center point.
31. The stent of paragraph 29, wherein each inner crown strut is straight along its length and substantially oriented in a side branch radial direction.
32. The stent of paragraph 29, the intermediate crown further comprising a plurality of intermediate crown inner turns and a plurality of intermediate crown outer turns, each intermediate crown strut connected at one end to an intermediate crown inner turn and at another end to an intermediate crown outer turn, the intermediate crown inner turns located closer to a side branch center point than the intermediate crown outer turns.
33. The stent of paragraph 32, wherein a first inner side branch connector is connected at one end to an inner crown outer turn and connected at the other end to an intermediate crown inner turn.
34. The stent of paragraph 32, wherein a first outer side branch connector is connected at one end to an outer crown outer turn and connected at the other end to an intermediate crown outer turn.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A balloon expandable stent in an unexpanded configuration comprising:
    a plurality of struts arranged to form a substantially cylindrical expandable framework, the struts defining a plurality of cells; and
    a side branch structure comprising:
        an outer crown comprising a plurality of outer crown struts arranged to form a closed loop, the outer crown defining a side branch area;
        an inner crown comprising a plurality of inner crown struts and inner crown turns arranged to form a closed loop, the inner crown turns comprising inner turns and outer turns, the struts and inner turns defining petals, the inner crown defining an inner side branch cell having a shape different from the shape of any other cell, the inner turns located closer to a centerpoint of the inner side branch cell than the outer turns; and
        a plurality of side branch connectors made from the same material as the inner crown, each side branch connector having a first end connected to an outer turn of the inner crown and a second end connected to the outer crown, each side branch connector comprising an inflection point, each side branch connector oriented such that said first end and said second end are not aligned in a side branch radial direction.

2. The stent of claim 1, wherein upon expansion of said side branch structure, the inner crown rotates about a center point of the side branch structure.

3. The stent of claim 1, the side branch structure in an unexpanded state defining a plurality of outer side branch cells, each outer side branch cell being partially bounded by at least one outer crown strut, at least one inner crown strut, a first side branch connector and a second side branch connector, wherein the shape of an outer side branch cell comprises the shape of another outer side branch cell rotated about a center point of the side branch structure.

4. The stent of claim 1, wherein a perimeter of the inner crown is equal to or longer than a perimeter of the outer crown.

5. The stent of claim 1, wherein the outer crown remains in said cylindrical expandable framework after expansion of said side branch structure.

6. The stent of claim 1, wherein at least a portion of a first side branch connector is oriented in a side branch non-radial direction when said side branch structure is unexpanded.

7. The stent of claim 6, wherein said first side branch connector reorients upon expansion of said side branch structure to have a length component oriented in a side branch radial direction.

8. The stent of claim 1, wherein a cross-sectional area of an inner crown strut is greater than a cross-sectional area of a side branch connector.

9. The stent of claim 1, wherein each petal rotates to unfold outwardly in a stent radial direction upon petal deployment.

10. The stent of claim 1, wherein each side branch connector comprises a first curved portion and a second curved portion located on opposite sides of said inflection point.

11. The stent of claim 1, wherein upon expansion of said side branch structure, the entire inner crown displaces outwardly from said cylindrical expandable framework in a stent radial direction.

12. A balloon expandable stent in an unexpanded configuration comprising:
- a plurality of struts arranged to form a substantially cylindrical expandable framework, the struts defining a plurality of cells; and
- a side branch structure comprising:
  - an outer crown comprising a plurality of outer crown struts arranged to form a closed loop, the outer crown defining a side branch area;
  - an inner crown comprising a plurality of inner crown struts and inner crown turns arranged to form a closed loop, the inner crown turns comprising inner turns and outer turns, the struts and inner turns defining petals, the inner crown defining an inner side branch cell having a shape different from the shape of any other cell, the inner turns located closer to a centerpoint of the inner side branch cell than the outer turns; and
  - a plurality of side branch connectors made from the same material as the inner crown, each side branch connector having a first end connected to an outer turn of the inner crown and a second end connected to the outer crown, each side branch connector comprising an inflection point;
  - wherein said plurality of side branch connectors comprises a first side branch connector having a length that is different from the length of a second side branch connector.

13. The stent of claim 1, wherein each inner crown outer turn is located an equal distance from the side branch center point.

14. The stent of claim 1, the outer crown further comprising a plurality of outer crown inner turns and a plurality of outer crown outer turns, each outer crown strut connected at one end to an outer crown inner turn and at another end to an outer crown outer turn, the outer crown inner turns located closer to a side branch center point than the outer crown outer turns, wherein each side branch connector is connected at the second end to an outer crown outer turn.

15. The stent of claim 14, wherein each side branch connector comprises a length that is greater than two outer crown struts.

16. A method comprising:
- providing the stent of claim 1;
- orienting the stent within a main bodily vessel with the side branch structure adjacent to a branch vessel; and
- expanding said side branch structure, wherein said inner crown displaces outwardly from said cylindrical expandable framework and into said branch vessel.

17. The method of claim 16, wherein the expanding step further comprises orienting an inflation device within an internal lumen of the stent adjacent to the side branch structure and inflating the inflation device to thereby cause the inner crown to displace outwardly.

* * * * *